US008329635B2

(12) United States Patent
Uggeri et al.

(10) Patent No.: US 8,329,635 B2
(45) Date of Patent: Dec. 11, 2012

(54) METHOD FOR THE PREPARATION OF SPECIFIC ANTIBODIES AGAINST SACCHARIDIC ANTIGENS

(75) Inventors: Fulvio Uggeri, Codogno (IT); Cristiana Campa, Siena (IT); Sergio Paoletti, Trieste (IT); Anna Coslovi, Trieste (IT); Alfonso Colombatti, Udine (IT); Carla Danussi, Udine (IT)

(73) Assignee: Bracco Imaging S.p.A., Milan (IT)

( * ) Notice: Subject to any disclaimer, the term of this patent is extended or adjusted under 35 U.S.C. 154(b) by 144 days.

(21) Appl. No.: 12/308,206

(22) PCT Filed: Jun. 19, 2007

(86) PCT No.: PCT/EP2007/056081
§ 371 (c)(1),
(2), (4) Date: Dec. 9, 2008

(87) PCT Pub. No.: WO2007/147823
PCT Pub. Date: Dec. 27, 2007

(65) Prior Publication Data
US 2009/0202580 A1    Aug. 13, 2009

Related U.S. Application Data

(60) Provisional application No. 60/815,158, filed on Jun. 20, 2006.

(30) Foreign Application Priority Data

Dec. 22, 2006   (EP) .................................... 06127025

(51) Int. Cl.
*A01N 61/00*   (2006.01)
*A61K 39/40*   (2006.01)
(52) U.S. Cl. ........................ 514/1; 424/137.1
(58) Field of Classification Search .................. None
See application file for complete search history.

(56) References Cited

FOREIGN PATENT DOCUMENTS

WO    WO 99/58978 A2    11/1999
WO    WO 99/58978 A3    11/1999

OTHER PUBLICATIONS

Kuduk et al (J Am Chem Sox, 1998, 120:12474-12485) teaches.*
Kuduk et al (J. Am. Chem. Soc., 1998, 120: 12474-12485).*
Domen et al (The Journal of Immunology, 1987, 139(10): 3195-3198).*
Kunz et al (Carbohydrate Research, 1990, 202: 207-223).*
PCT Search Report for PCT/EP2007/056081, mail date Sep. 7, 2007.
PCT Written Opinion for PCT/EP2007/456081, mail date Sep. 7, 2007.
E. Kagan et al., Comparison of antigen constructs and carrier molecules for augmenting the immunogenicity of the monosaccharide epithelial cancer antigen Tn., Cancer Immunology, Immunotherapy, vol. 54, No. 5, May 2005, pp. 424-430, XP019333116, Germany.
H. Kunz et al., Synthesis of glycopeptides with the TN and T antigen-structures, and their coupling to bovine serum albumin, Carbohydrate Research, vol. 202, 1990, pp. 207-223, XP002447217.
K. Dahlenborg et al., Human monoclonal antibodies specific for the tumour associated Thomsen-Friedenreich antigen, International Journal of Cancer, vol. 70, No. 1, Jan. 6, 1997, pp. 63-71, XP002447218, USA.
P. Domen et al., Cationization of protein antigens, III. Abrogation of oral tolerance, The Journal of Immunology, vol. 139, No. 10, Nov. 15, 1987, pp. 3195-3198, XP002447216, USA.
S. Kudak et al., Synthetic and immunological studies on clustered modes of mucin-related Tn and Tf O-linked antigens: The preparation of a glycopeptides-based vaccine for clinical trials against prostate cancer, Jounal of the American Chemical Society, vol. 120, 1998, pp. 12474-12485, XP002956518, USA.
T. Toyokuni et al., Synthetic carbohydrate vaccines: Synthesis and immunogenicity of Tn antigen conjugates., Bioorganic & Medicinal Chemistry, vol. 2, No. 11, 1994, pp. 1119-1132, XP000938458, U.K.
Dziadek, Sebastian et al., Agnew. Chem. Int. Ed., 2005, vol. 44, pp. 7624-7630.
Kunz, Horst et al., Agnew. Chem. Int. Ed. Engl., 1986, vol. 25, pp. 360-362.
Kunz, Horst et al., Environmental Health Perspectives, 1990, vol. 88, pp. 247-249.
Japanese associate, Aoyama & Partners, Jun. 26, 2012 letter reporting issuance of Jun. 19, 2012 Office Action for JP2009-515859 application.

* cited by examiner

*Primary Examiner* — Sean Aeder
(74) *Attorney, Agent, or Firm* — M. Caragh Noone (57) ABSTRACT

The present invention relates to new compounds useful for the stimulation of the production of antibodies. Said compounds comprises a saccharidic tumor antigen and a polymeric scaffold. The present invention also encompasses conjugated compounds useful in ELISA assay for the selection of antibodies against saccharidic antigens.

15 Claims, 3 Drawing Sheets

METHOD FOR THE PREPARATION OF SPECIFIC ANTIBODIES AGAINST SACCHARIDIC ANTIGENS

This application is the national stage application of corresponding international application number PCT/EP2007/056081 filed Jun. 19, 2007, which claims priorities to and the benefits of both the U.S. provisional application No. 60/815,158, filed Jun. 20, 2006 and European application no. 06127025.2, filed Dec. 22, 2006, all of which are hereby incorporated by reference.

The present invention finds application in the field of immunodiagnosis and immunotherapy and, more in particular, it relates to compounds useful in the preparation of antibodies directed against Tumor Associated Carbohydrate Antigens.

BACKGROUND

Carbohydrates are known to exert an important role in several biological and physiological pathways. It has been found, in fact, that they may contribute to the protein stability or resistance to degradation, to the regulation of intracellular signalling and targeting of glycoproteins to membranes or cell organelles, and to have implications in immunological recognition [see, as a general reference, Varki, A.; *Glycobiology* 1993, 3, 97-130, Bertozzi, C. L., Kiessling, L. L.; *Science* 2001, 291, 2357-64, Angeloni, S.; *Glycobiology* 2005, 15 (1), 31-41)].

In addition to that, several studies and research projects have discovered that carbohydrates and derivatives thereof, for instance glycans, take also part in some neoplastic modifications of cells. In fact, [as reported by Hakomori, S.; Chapter 4 in Montreuil, J., Vliegenthart, J. F. G., Schachter, H. (editors) Glycoproteins and disease. Elsevier, Amsterdam, 1996 or by Kobata A.; Cancer cells and metastasis. Chapter 3 in Montreuil, J., Vliegenthart, J. F. G., Schachter, H. (editors) Glycoproteins and disease. Elsevier, Amsterdam, 1996 or by Kumamoto et al in *Biochemical and Biophisical Research Communications* 1998, 247, 514-7 or by Hakomori, S.; *PNAS* 2002, 99 (16), 10231-33], it has been observed that glycans, known to be present on cell membranes, usually exhibit structural modifications, for instance a high degree of branching in cancer cell membranes over normal cell membranes.

Likewise, besides any structural modification, it has also been observed an altered composition in membrane carbohydrates with respect to normal cells.

As an additional example of a saccharidic moiety playing a role in neoplastic processes there is, for instance, sialic acid (see The Merck-Index; XIII Ed.; No. 8558), a 9-carbon atom amino sugar being a member of neuraminic acid related compounds. There has been observed, in fact, that the high metastatic activity of certain tumoral forms may be well correlated with an increased concentration of sialic acid in cell membranes, thus yielding to a reduced adhesive capability of the extra-cellular matrix cells in metastatic phenomena (see, for a reference, Varki, A. et al *Essentials of glycobiology*. Cold Spring Harbor Laboratory Press, Cold Spring Harbor, N.Y. 1999).

Additionally, for instance as reported by Sames, D. et al in *Nature* 1997, 389, 587-91 or by Dwek, M. V. et al. (*Clinica Chimica Acta* 1998, 271, 191-202) or by Burchell et al (*Glycobiology* 1999, 9 (12), 1307-11) or by Taylor-Papadimitriou et al. (*Biochim. Biophys. Acta* 1999, 1455, 301-13) or by Hanisch et al (*Glycobiology* 2000, 10 (5), 439-49) or by Schuman, J. et al (*Glycoconjugate Journal* 2000, 17, 835-48) within complex saccharidic compounds, a highly glycosilated glycoprotein like altered MUC1, which shows a high number of O-glycosidic residues and that provides a protective layer on epithelial surfaces and it is involved in cell-cell interactions, signalling, and metastasis (see, for a reference Parry S, Silverman H S et al., Biochem. Biophys. Res. Commun. 2001; 11; 283(3): 715-20), seems to contribute to the metastatic potential of the neoplastic cells.

Though numerous molecular alterations have been found to be associated with each single developing or progressing phase of a tumor, the exact relationship among them is not yet completely understood.

The phenotypic alterations in saccharides found to characterize a neoplasia, are generally known as Tumor Associated Carbohydrate Antigens (hereinafter shortly referred to as TACAs).

The epitopes Gal-β-1→3-GalNAc-α-O.Ser/Thr and GalNAc-α-O.Ser/Thr (see the chemical structures below), commonly referred to as TF and Tn respectively, are among the most widespread known TACAs.

TF antigen (Gal-β-1 ⟶ 3-GalNAc-α-O. Ser/Thr)

Tn antigen (GalNAc-α-O. Ser/Thr)

As from the above reported formulae, the Tn immunodeterminant group is a GalNAc residue α linked to the hydroxyl group of serine or threonine, which appears in the amino-terminal region of glycoproteins. In its turn, Gal-β-1→3-GalNAc-α-O.Ser/Thr (TF antigen) is then formed by the action of the enzyme β-galactosyltransferase, which adds a galactose residue, taken from a Gal-nucleotide, to a Tn residue.

The occurrence of these antigens in normal tissues has been investigated in order to verify their specificity toward pathological tissues (see, for example, Cao, Histochem. Cell Biol. 1996, 106, 197-207).

Moreover, TF and Tn antigens were found to be overexpressed in immunoreactive form, to a significant extent, in about 90% of carcinoma tissues (see, for a reference, Springer, G. F.; *Science* 1984, 224, 1198-206) and their relative proportion in human carcinomas frequently correlates with the carcinoma's aggressiveness itself.

The results of several studies also suggested that at the early stages of the metastatic process, TF and Tn antigens both play a key role in adhesion phenomena between the tumoral cells and the adjacent normal cells (see, for a reference, Kischikawa et al, in Jpn. J. Cancer Res. 1999, 90, 326-32).

The isolation and structural identification of carbohydrate antigens specifically over-expressed in cancer cells, and thus of TF and Tn, represents a first step for the development of a strategy for the therapy and diagnosis of neoplastic diseases: the carbohydrate-based immunotherapy and immunodiagnosis (see, for instance, Allen in J. Aim Chem. Soc., 2001, 123, 1890-7).

It is well known in the art that immunotherapy involves the stimulation of the natural body defenses, i.e. immunosystem, against harmful agents such as microorganisms, pollutants, chemicals, foods and the like. Therefore, it has been envisaged that cancer cells, characterized by an altered expression of TACAs on their membrane, might represent the target of the human or animal immunosystem.

There was found that the stimulation of the immunosystem through suitable tumoral antigens such as, for example Tn or TF antigens, could be a promising therapeutic tool against tumor.

Toyokuni et al. (see, for a reference, Bioorg. Med. Chem. 1994, 2, 119-32) describes the preparation of totally synthetic carbohydrate vaccines by the use of monomeric, dimeric and trimeric Tn antigens further conjugated with Ovine Serum-Albumin, Starbust® dendrimer and tripalmitoyl-S-glyceryl-cysteinylserine ($P_3CS$).

Lo-Man et al. (see, for example, J. Immunol. 2001, 166, 2849-54) discloses the development of a fully synthetic immunogen called multiple antigenic glycopeptide and based on a dendrimeric lysine core with four arms.

Kuduk et al. (see, for a reference, J. Am. Chem. Soc. 1998, 120, 12474-12485) describes the use of KLH, BSA and a lipopeptide (pam) for the clusterization of Tn and TF antigens, while Dziadek et al. (Angew. Cem. Int. Ed. 2005, 44, 7624-7630) discloses a similar approach for the preparation of compounds comprising TACAs and BSA and MUC1 peptides.

Kagan et al. (see, for a reference, Cancer Immunol. Immunother. 2005, 54, 424-430) describes the tests made on several Tn conjugates: Tn monosaccharide, Tn(c) prepared on a triple threonine backbone and Tn prepared on a partially or fully glycosylated MUC1 backbone.

Among the major limitations of the above reported conjugated compounds, however, is the fact that when used as vaccines, they lead to the production of poor quantities of the desired antibodies and, also, that an aspecific mixture of the same is finally recovered (for example, see Grigalevicius et al, Bioconjugate Chemistry, 2005, 16, 1149-1159).

We have now found novel conjugated compounds of TF and Tn antigens that may be used as vaccines in the therapy against tumors. The conjugated compounds of the invention, in addition, allow to overcome the above drawbacks of the TACAs conjugated compounds of the prior art.

DESCRIPTION OF THE INVENTION

It is therefore a first object of the present invention a compound comprising a plurality of Tn or TF antigens conjugated to a polymeric scaffold selected from the group consisting of cationized bovine serum albumin (cBSA), alginate or dextran, either directly or through any suitable linker.

In the present description, and unless otherwise provided, with the term polymeric scaffold we intend any of the above scaffolds like cBSA, alginate or dextran having polymeric structure.

Among the polymeric scaffold within the scope of the present invention, there is Bovine Serum Albumin (BSA), a highly immunogenic protein, that can be further modified through the introduction of alkylamino groups at the aspartic acid or glutammic acid residues, thus obtaining cationized Bovine Serum Albumin (cBSA). According to the present invention, the molecular weight of cBSA is approximately comprised between about 65 to about 77 KDa.

For a general reference to cBSA and its preparation see, for instance, Domen et al. in J. Immunol. 1987, 139, (10), 3195-8.

Alginate is a mixture of polysaccharidic chains of different-molecular weight (see, as an example, The Merck Index, XIII Ed., No. 239).

Typically, according to the present invention, the molecular weight of alginate may range from about 130,000 to about 170,000 and, more preferably, from about 140,000 to about 160,000.

Finally, for a general reference to dextran see, for instance, The Merck Index, XIII Ed., No. 2965.

The preferred conjugated compounds of the present invention comprise cBSA and alginate and, even more preferably, they comprise cBSA.

As formerly reported, the above polymeric scaffolds are conjugated either directly, that is through a covalent bond, or by means of a suitable linker, to a plurality of Tn or TF antigens.

Suitable examples of linkers may comprise either straight or branched, synthetic or naturally occurring amino acids and derivatives thereof including, for instance, suitable peptides or carbohydrates, other similar linkers being within the knowledge of the skilled person.

More preferably, the said amino acids or peptides may comprise from 2 to about 10 carbon atoms.

According to a preferred embodiment of the invention, however, the conjugated compounds comprise the above antigens directly linked to the selected scaffold.

As far as both Tn and TF antigens are concerned, whose structural formula have been above reported, they are linked to the rest of the moiety (e.g. scaffold) through carboxamido bonds, that is to say through any of their amino or carboxy groups.

With the term "a plurality of Tn or TF antigens" we intend, unless otherwise provided, that more than one of the said antigens are linked, directly or through a suitable linker, to the polymeric scaffold.

Typically, the number of antigens linked to the polymeric support, within the conjugated compounds of the invention, may vary to a great extent according to the number of monomeric units forming the polymeric scaffold itself and bearing suitable reactive functional groups (e.g. amino, carboxy) as well as from the operative experimental conditions being adopted in the synthesis of the conjugated compound.

In particular, in the case of the conjugated compounds of the invention comprising cBSA, from about 5 to about 30 moieties of Tn or of TF antigens, for instance from about 10 to about 20 moieties of Tn or of TF antigens, may be linked to each cBSA molecule.

Likewise, in the case of the conjugated compounds comprising alginate, from about 200 to about 250 moieties of Tn or of TF antigens, for instance from about 220 to about 230 moieties of Tn or of TF antigens, may be linked to each alginate molecule.

According to a preferred embodiment, the present invention refers to a conjugated compound comprising cBSA directly linked to a plurality of Tn antigens.

According to another preferred embodiment, the invention relates to a conjugated compound comprising alginate directly linked to a plurality of Tn antigens.

According to an additional object of the invention, herewith provided there is a process for the preparation of the above reported conjugated compounds, said process comprising the steps of:

1) dissolving any one of the polymeric scaffolds in a suitable buffered aqueous solution;
2) adding to the solution of step (1) a condensing agent and a suitable amount of the selected Tn or TF antigen, each of which is optionally connected to a suitable linker, in the presence of a condensing agent; and
3) mixing and stirring the resulting solution from step (2) for a suitable period of time and recovering the obtained product.

The above process, and any variant thereof, is carried out as per step (1) in suitable aqueous buffers, such as 2-morpholino-ethansulphonic acid (MES); suitable concentration is, for example 25 mM, while suitable pH is comprised between about 4.5 to about 7, preferably being 6.5.

As far as step (2) is concerned, the amount of selected antigen is the one that allows the antigen and the scaffold to react in the expected molar ratio, so as to obtain the desired conjugated compound of the invention.

The above reaction is carried out in the presence of any suitable condensing agent conventionally adopted in the formation of carboxamido bonds. Preferably, said condensing agent is N-Hydroxysuccinimide (NHS), either alone or in combination with 1-ethyl-3-(3-dimethylaminopropyl)carbodiimide (EDC).

The above mentioned condensing agents are preferably used in a slight stoichiometric excess.

From the above, it is clear to the skilled person that the linker, whenever present, may be already bonded (e.g. connected) to the selected antigen before the same undergoes coupling with the scaffold or, alternatively, it may be bonded (e.g. connected) to the scaffold, at first, so that the resulting intermediate compound is then coupled with the selected antigen.

In this respect, both of these optional variants are within the scope of the present invention.

In addition, as the antigen and the scaffolds are coupled, either per se or by means of any suitable linker, through the formation of carboxamido bonds, e.g. —CONH— or —NHCO—, it is clear to the skilled person that any other reactive group optionally present in any one of the antigen, the scaffold or even the linker itself, and which may be susceptible to react under the above operative conditions so as to give rise to unwanted side products, need to be properly protected/deprotected according to well known methods.

According to the present invention, the recovery of the final product in step (3) is performed by conventional methods including, for example, dialysis and freeze-drying. Within the present process, and as per any variant thereof, either the reactants as well as any of the starting materials including the selected antigen and the scaffold, each of which being optionally coupled to a linker, and the linker per se, are all known compounds or they can be prepared according to conventional methods known in the art.

The determination of the substitution degree of the compounds of the present invention, that is the number of Tn or TF antigens residues linked to each scaffold, is carried out according to known methods.

As an example, the determination of the substitution degree of the compounds of the present invention comprising cBSA is carried out via enzymatic reaction with the use of the enzyme α-N-Acetylgalactosaminidase from *Acremonium* sp. according to the experimental conditions indicated by the supplier of the enzyme [Seikagaku (Tokyo, Japan)]. More in detail, for example, as for Tn antigen, the hydrolysis is performed by incubating 0.25 ml of the substrate mixture containing Tn antigen with 0.05 ml of enzyme (having an activity of about 13 U/ml) in citrate buffer for 2 hours at pH 4.5 and at 37° C. The reaction is then quenched by the addition of 0.2 M borate buffer at pH 9.8. The quantification of the resulting sugar residue, i.e. N-Acetylgalactosamine (GalNac) from Tn antigen, is made by capillary electrophoresis as further described in the Materials and Method section. In turn, the substitution degree of the compounds of the present invention comprising alginate or dextran is determined by automated elementary analysis carried out on a lyophilized sample of the conjugated compound.

The results of the determination of the substitution degree (see Examples 3 and 4 of the Experimental Section), i.e. the number of Tn or TF antigens residues linked to each scaffold, are then expressed as a percentage. Therefore, for example, a 15% substitution degree of alginate means that 15 over 100 repetitive monosaccharide units of alginate are linked to one molecule of Tn or TF antigen.

As formerly reported, the conjugated compounds of the invention may find application in therapy and prophylaxis and, more in particular, they may be used as vaccines against tumors.

It is therefore a further object of the invention, a pharmaceutical composition comprising a conjugated compound wherein a plurality of Tn or TF antigens is linked to a polymeric scaffold selected from the group consisting of cationized bovine serum albumin (cBSA), alginate or dextran, either directly or through any suitable linker, together with pharmaceutically acceptable excipients including, solvents, carriers, buffers, stabilizers and the like, as per the general pharmaceutical practice.

In general, any suitable excipient may be properly included in the pharmaceutical compositions of the invention, the preparation of which may be accomplished according to general methods well known to the skilled person in the art.

It is therefore a further object of the present invention a compound comprising a plurality of Tn or TF antigens conjugated to a polymeric scaffold selected from the group consisting of cationized bovine serum albumin (cBSA), alginate or dextran, either directly or through a suitable linker, for use in therapy or prophylaxis.

Additionally, a further object of the invention is represented by a method for the treatment or the prophylaxis of tumors, which method comprises the administration to a mammal of a suitable amount of a conjugated compound of the invention wherein a plurality of TF or Tn antigens is linked to a polymeric scaffold selected from the group consisting of cationized bovine serum albumin (cBSA), alginate or dextran, either directly or through any suitable linker, or of any pharmaceutical composition thereof.

For the intended purpose, suitable amounts of the conjugated compounds of the invention are those typically employed for therapeutic or prophylactic purposes comprising the administration of antigens and derivatives thereof and they may be determined according to a selected suitable therapeutic protocol.

Accordingly, it is an additional object of the invention, the use of a compound comprising a plurality of Tn or TF antigens conjugated to a polymeric scaffold selected from the group consisting of cationized bovine serum albumin (cBSA), alginate or dextran, either directly or through any suitable linker, in the preparation of a medicament or vaccine for the treatment or prevention of tumors.

According to an additional embodiment, the conjugated compounds of the invention may also be used for the preparation of specific antibodies against Tn or TF antigens. Typically, the aforementioned antibodies may be prepared by means of well known methods employed in the production of monoclonal antibodies (hereinafter referred to as mAbs).

For the purpose of the present invention, experiments with animals involved normal mice, which were used solely to produce mAbs. They have been housed in animal facilities according to the standards for animal care established by national regulations and maintained in accordance with individual institutional guidelines under approved authority protocols. They also have been regularly checked by veterinarians and handled by qualified animal care takers within an authorized animal facility.

For a general reference to the preparation of monoclonal antibodies see, for instance, Köhler, G., Milstein, C.; Nature 1975, 256, 495-7.

As an example, the claimed method for the preparation of the given antibodies may thus comprise the following steps:
1) BALB/c mice immunization;
2) sacrifice of the animals and spleen excision;
3) immortalization antibody-producing cells by somatic cell hybridization (fusion);
4) selection of the hybrid cells in HAT culture medium;
5) screening by ELISA assay to obtain the most specific clones; and
6) subcloning.

Immunization, as per step (1), is performed by the injection of the conjugated compound of the present invention. Preferably, the conjugated compound is the one wherein a plurality of Tn antigens is directly linked to cBSA.

Steps 2), 3), 4) and 6) are performed according to known methods.

In particular, according to the present invention, as far as step (5) is concerned, the Enzyme Linked Immuno Sorbent Assay (better known as ELISA) comprises the use of a solid phase onto which the selected Tn or TF antigens, corresponding to that used for immunization when conjugated with the scaffolds of the invention, is properly immobilized.

More in particular, the polymeric scaffold is a biotinylated polymeric scaffold, so that it can be linked/immobilized onto the solid support through a streptavidin/biotin linkage. ELISA is a well-know assay for the detection and quantification of substances, for example proteins, antibodies and hormones. The first step of ELISA requires the immobilization of specific antigens onto an ELISA plate; then, a sample containing the antibodies to be selected according to the present invention is added to the solid phase and incubation is allowed so that a complex between the immobilized antigens and the complementary antibodies may form. Washing is then carried out in order to remove unbound materials. The further step includes the addition of a secondary antibody directed to the formed complex and linked to a suitable enzyme [the most commonly used enzymes are horseradish peroxidase (HRP) and alkaline phosphatase (AP)].

Finally, as an example, the subsequent addition of a suitable chromogen will result in a variation of colour intensity depending upon the quantity of antibodies bound to the immobilized antigen and, as far as this latter variation is assessed, to the quantity of antibodies present in the sample.

For a general reference to the ELISA technique, as per the present invention, see the following Experimental Section.

We have observed, in particular, that the immobilization of the selected antigen onto the solid phase, for ELISA purpose, may be conveniently carried out by immobilizing the biotinylated conjugated compound of the invention. In this respect, the immobilization of the antigen-biotinylated alginate conjugate proved to be particularly selective in detecting antibodies originating from the inoculation of any of the conjugated compounds of the invention themselves.

In other words, when immunization and antibodies preparation follow proper inoculation to mice of the selected conjugated compound of the invention, for instance of the conjugated between Tn and cBSA, the ELISA test may be conveniently performed by adding the sample containing the antibodies thus produced to the solid phase comprising the biotinylated conjugated compounds of the invention, preferably the biotinylated alginate conjugate with that same TACA, that is to say, Tn antigen.

From the above, it is clear to the skilled person that analogous consideration may apply when referring to TF antigens and conjugated compounds thereof.

Therefore, it is another object of the present invention a compound comprising a plurality of Tn or TF antigens conjugated to a biotinylated polymeric scaffold selected from the group consisting of biotinylated alginate, biotinylated cationized bovine serum albumin (biotinylated cBSA) or biotinylated dextran, either directly or through any suitable linker.

Preferably, the biotinylated polymeric scaffold is biotinylated alginate.

In this respect, cBSA, alginate and dextran are defined as formerly reported.

Likewise, the number of Tn or TF antigens linked to the biotinylated scaffolds of the present invention is as defined above.

Biotin (see The Merck Index, XIII Ed., No. 1231) is a naturally occurring growth factor known to play a role in carboxylation reactions with proteins or polypeptides.

As biotin selectively binds to streptavidin, which is especially used for the in vitro preparation of solid beds, biotin may be usefully linked to molecules to be immobilized onto said solid phases in separation as well as in purification techniques.

Among biotin derivatives, N-(+)-biotinyl-L-lysine hydrazide may be usefully employed in the biotinylation of polymeric scaffolds. In particular, it is a commercially available compound, having the chemical formula shown below:

N-ε-(+)-biotinyl-L-lysine hyrazide

The linkage of biotin to polymers, i.e. cBSA, alginate or dextran, occurs randomly through any of the carboxy groups of these polymeric compounds.

As for the preparation of the conjugated compounds of the present invention wherein the polymeric scaffold is a biotinylated polymeric scaffold, said process includes the steps of:
1) dissolving any one of the polymeric scaffolds in a suitable buffered aqueous solution;
2) adding to the solution of step (1) a suitable amount of biotin or of a biotinylating agent, in the presence of a suitable condensing agent;
3) adding to the solution obtained from step (2) a suitable condensing agent and a suitable amount of the selected Tn or TF antigen, each of which is optionally connected to a suitable linker; and
4) mixing and stirring the resulting solution from step (3) for a suitable period of time and recovering the obtained product.

As for the above process, a suitable amount of biotin or a biotinylating agent is within the knowledge of the skilled person so as to get the desired biotinylated polymer.

However, for a specific reference to the operative conditions being employed in the process of the invention, and details thereof, see the following Experimental Section.

A preferred condensing agent is, for instance, NHS used alone or in combination with EDC.

It is therefore an additional object of the invention the use of a conjugated compound comprising Tn or TF antigens linked to biotinylated alginate, biotinylated cBSA or biotinylated dextran, properly immobilized onto a solid phase, in an ELISA test for the detection of antibodies produced upon immunization techniques wherein Tn or TF are those same Tn or TF antigens respectively conjugated with cBSA, alginate or dextran.

According to an embodiment of the invention, particularly preferred is the use of a conjugated compound comprising Tn or TF antigens linked to biotinylated alginate, properly immobilized onto a solid phase, in the detection through ELISA test of antibodies produced upon immunization techniques and comprising those same Tn or TF antigens conjugated with cBSA, alginate or dextran.

Typically, unless otherwise provided, proper immobilization onto the solid phase of the Tn or TF antigen conjugated with the biotinylated polymer may comprise coating a microtiter ELISA plate wells with streptavidin, filling the wells with the selected conjugate between the biotinylated polymer and Tn or TF and leave incubating for a suitable period time.

The above operative conditions are well known in the art and details thereof are reported in the Experimental Section.

The antibodies thus produced and selected according to the present invention may also be used for therapeutic purposes.

Additionally, as they selectively target specific tumor sites or tissues, they may be properly functionalized, according to known methods, with diagnostically or therapeutically active compounds.

In fact, as they selectively attack and bind to tumoral cells expressing on their surface Tn and/or TF antigens, they may also act as carriers to bring therapeutically active moieties on the tumoral sites or tissues or to bring at those sites or tissues diagnostic moieties for enabling the visualization.

Typically, functionalization with therapeutically or diagnostically active compounds may comprise reacting the said antibodies with given antitumoral drugs or detectable labels known in the art.

From the above, it is clear to the skilled person that the antibody and the therapeutically or diagnostically active moiety may be linked to each other either directly or, alternatively, through any suitable linker or spacer known in the art.

These linkers may include, but are not restricted to, substituted or unsubstituted alkyl chains, polyethylene glycol derivatives, amino acid spacers, sugars or aliphatic or aromatic spacers commonly known in the art.

Suitable examples of diagnostic moieties according to the present invention include, for instance, paramagnetic metal chelates suitable for magnetic resonance imaging (MRI), radiolabels suitable for X-ray imaging, ultrasound microspheres or liposomes suitable for ultrasound detection or optical imaging dyes.

Among the paramagnetic chelates, the preferred metals elements are those having atomic number ranging between 20 and 31, 39, 42, 43, 44, 49 and between 57 and 83. More preferred are paramagnetic metal ions selected from the following: $Fe(2+)$, $Fe(3+)$, $Cu(2+)$, $Ni(2+)$, $Rh(2+)$, $Co(2+)$, $Cr(3+)$, $Gd(3+)$, $Eu(3+)$, $Dy(3+)$, $Tb(3+)$, $Pm(3+)$, $Nd(3+)$, $Tm(3+)$, $Ce(3+)$, $Y(3+)$, $Ho(3+)$, $Er(3+)$, $La(3+)$, $Yb(3+)$, $Mn(3+)$, $Mn(2+)$ wherein $Gd(3+)$ is the most preferred. The organic chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclotetradecane-1,4,7,10-tetraacetic acid (DOTA), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof, the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,1,1-(methyl tetraacetic acid); derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl) aminomethylbenzene (MECAM), (4S)-4-(4-ethoxybenzyl)-3,6,9-triscarboxylatomethyl)-3,6,9-triazaundecandioic acid-disodium (EOB-DTPA), N,N-bis[2-[bis(carboxymethyl) amino]ethyl]-L-glutamic acid (DTPA-GLU), N,N-bis[2-[bis(carboxymethyl)amino]ethyl]-L-lysine (DTPA-LYS), the DTPA mono- or bis-amide derivatives, such as N,N-bis[2-[carboxymethyl[(methylcarbamoyl)methyl]-amino]ethyl] glycine (DTPA-BMA), 1,4,7,10-tetraazacyclododecan-1,4,7-triacetic acid (DO3A), 10-(2-hydroxypropyl)-1,4,7,10-tetraazacyclododecan-1,4,7-triacetic acid (HPDO3A), 4-carboxy-5,8,11-tris(carboxymethyl)-1-phenyl-2-oxa-5,8, 11-triazamidecan-13-oic acid (BOPTA), 2-methyl-1,4,7,10-tetraazacyclododecan-1,4,7,10-tetraacetic acid (MCTA), (α,α',α'',α''')-tetramethyl-1,4,7,10-tetraazacyclododecan-1, 4,7,10-tetraacetic acid (DOTMA), 3,6,9,15-tetraazabicyclo [9.3.1]pentadeca-1(15),11,13-triene-3,6,9-triacetic acid (PCTA) and 6-[bis(carboxymethyl)amino]-tetrahydro-6-methyl-1H-1,4-diazepine-1,4(5H)-diacetic acid (AAZTA) and derivatives thereof, as per the international patent application WO 03/008390 incorporated herein by reference.

Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, all of which are hereby incorporated by reference.

The above compounds, in particular those intended for diagnostic applications, and, even more particularly, those to be used for MRI, may all be prepared according to conventional methods known in the art.

Figure 1:
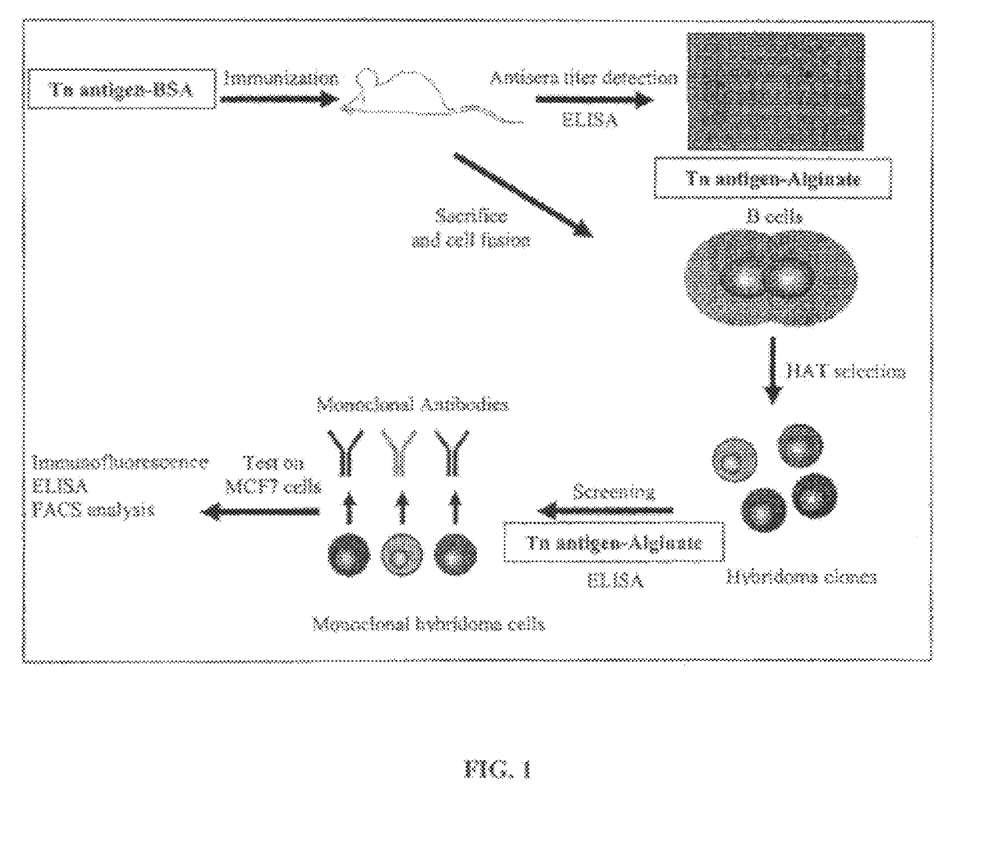
FIG. 1 illustrates the monoclonal antibodies production technique.
Figure 2:
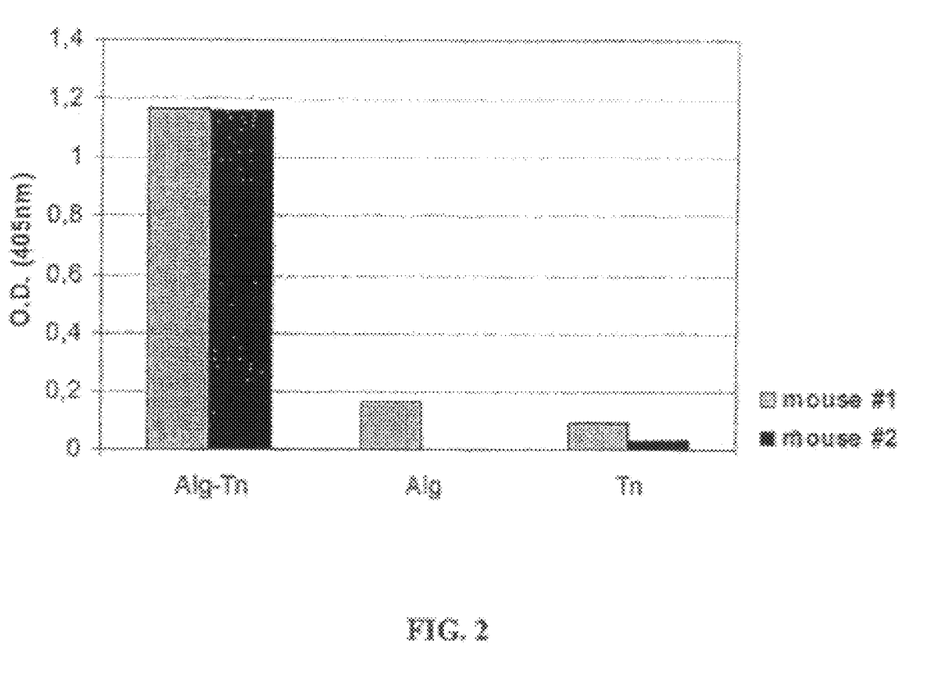
FIG. 2 shows the ELISA result of mouse "#1" and mouse "#2" serum after Tn-cBSA immunization tested on biotinylated alginate-Tn conjugated compound (Alg-Tn); alginate (Alg) and Tn antigen (Tn) are the used references.
Figure 3:
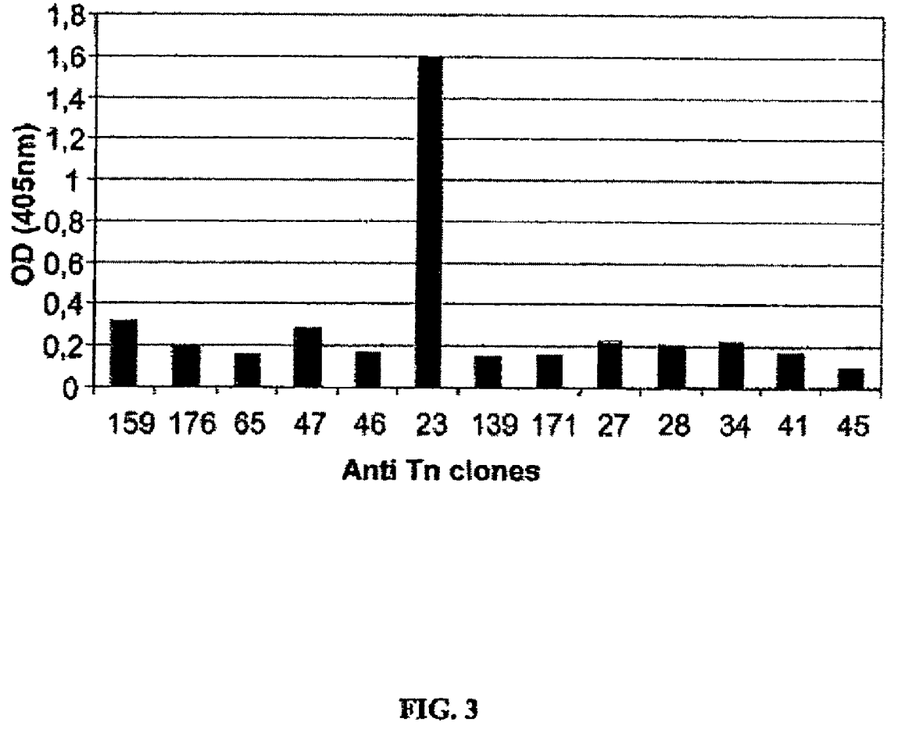
FIG. 3 shows an example of anti Tn hybridoma selection. In the graph the absorbance values of clone supernatants tested on biotinylated alginate-Tn conjugated compound are reported.

The following Examples will now disclose the present invention in more detail; other similar applications, even if not explicitly encompassed, are deemed to be within the scope of the present application.

EXPERIMENTAL SECTION

Materials and Methods

N-Hydroxysuccinimide (NHS), N-Acetylgalactosamine, 2-aminobenzoic acid (2-AA), sodium cyanoborohydride and biotin were from Sigma Chemical Co. (St. Louis., MO), Nε-(t)-biotinyl-L-lysinehydrazide, 1-ethyl-3-(3-dimethylaminopropyl)carbodiimide (EDC) and 2-morpholinoethanesulphonic acid (MES) monohydrate were from Fluka (Buchs, Switzerland), α-N-Acetylgalactosaminidase from *Acremonium* sp. was from Seikagaku (Tokyo, Japan), PBS (Phosphate-buffered saline; Cambrex Bio Science, Verviers, Belgium), Tween 20 (Sigma-Aldrich, St. Louis, Mo.), Ovalbumin (Sigma-Aldrich, St. Louis, Mo.) ABTS peroxidase substrate (Sigma-Aldrich, St. Louis, Mo.), anti mouse IgG-Peroxidase conjugated (Amersham Biosciences, Freiburg, Germany), Streptavidin (Sigma-Aldrich, St. Louis, Mo.).

Capillary Electrophoresis

High-performance capillary electrophoresis system was from Hewlett-Packard (Agilent, Waldbronn, Germany), Model HP3DCE, with HP Chemstation software.

Derivatization of GalNAc (standard or arising from hydrolysis of BSA-Tn) with 2-AA was carried out by mixing an aqueous solution of the sugar with the derivatizing solution (0.25 M 2-AA, 0.159 M sodium cyanoborohydride in 99% methanol and 1% acetic acid). The solution was heated at 60° C. for 5 hours. Before capillary electrophoresis analysis, the samples were diluted five times in water.

The analysis conditions are reported in Table A. Before each run, a capillary wash run with sodium hydroxide (2 min, 985 mbar) and with working buffer (4 min, 985 mbar) was performed.

TABLE 1

HPLC-UV experimental conditions
HPLC-UV

| Column | Synergy Polar (4.6 × 250 mm; 5 μm) from Agilent |
|---|---|
| Column temperature | RT or 45° C. (see text for details) |
| Mobile phase | Eluent A: $CH_3OH$ |
| | Eluent B: 5 mM $CH_3COONH_4$ pH 3.5 |
| Elution profile | 0-8': 3% A, 97% D; 13': 40% A, 60% B, |
| | 20': 90% A, 10% B; 38': 90% A, 10% B; 45': |
| | 3% A, 97% B |
| Flow rate | 1 mL/min |
| Injection volume | 10 μL |
| Detection with PDA detector | Run time: 30 min |
| | Scan wavelenght: 190-800 nm |
| | Channel A: 195 nm |

Instruments: HPLC-UV Merck-Hitachi equipped with a L-6200. Pump, an AS-200A Autosampler and a L-4500A Diode Array Detector. Data acquisition and analysis was performed by D-700 Chromatography Data Station software (Merck-Hitachi).

TABLE 2

HPLC-MS experimental conditions
HPLC-MS

| Column | Synergi Polar - RP 80A (2.0 × 250 mm; 4 μm) from Phenomenex |
|---|---|
| Column temperature | 45° C. |
| Mobile phase | Eluent A: $CH_3OH$ |
| | Eluent B: 5 mM $CH_3COONH_4$ pH 3.5 |
| Elution profile | 0-8': 3% A, 97% D; 13': 40% A, 60% B, |
| | 20': 90% A, 10% B; 38': 90% A, 10% B; 45': |
| | 3% A, 97% B |
| Flow rate | 200 μL/min |
| Injection volume | 10 μL |
| Detection with PDA detector | Run time: 45 min |
| | Scan wavelenght: 200-500 nm |
| | Channel A: 195 nm |
| Detection with MS detector | Run time: 45 min |
| | ESI voltage: 5 kV |
| | Polarity: positive |
| | Capillary temperature: 250° C. |
| | Sheath gas nature and flow: $N_2$ at 60 unit |
| | Auxiliary gas nature and flow: not used |
| | Capillary voltage: 46 V |
| | Tube lens offset: 55 V |
| | Mass range: 50-2000 |

Instrument: HPLC SURVEYOR Thermo Finnigan system equipped with MS Pump, Autosampler and PDA Detector, coupled with a LCQ DECA XP Plus Thermo Finnigan mass spectrometer with Electrospray Ionisation (ESI). The Xcalibur software was used for managing system and data.

Example 1

Preparation of cBSA-Tn Conjugated Compound

Tn antigen (1 mg) and cBSA (2 mg) were dissolved in a solution containing MES buffer (0.2 M), pH 6; EDC and NHS were added in a slight stoichiometric excess, and the mixture was stirred for 2 hours. The solution was then dialyzed and freeze-dried and the title compound was recovered accordingly.

By working in analogous way and by using any suitable antigen and any polymeric scaffold of the invention, the following compounds can be obtained:
-alginate-Tn conjugated compound;
-dextran-Tn conjugated compound;
-cBSA-TF conjugated compound;
-alginate-TF conjugated compound;
-dextran-TF conjugated compound.

Example 2

Preparation of Biotinylated Alginate-Tn Conjugated Compound

1) Biotinylation of Alginate

Alginate isolated from *Laminaria hyperborean* was provided by Protan A/S (Norway) and was purified by precipitation in isopropanol. 30 mg (0.15 mmol-repetitive unit) of alginate were dissolved in 10 mL of MES buffer (0.2 M) at pH 6. Then, EDC and NHS are added in a slight stoichiometric excess; N-ε-(+)-biotinyl-L-lysinehydrazide was then added (3.2 mg) and the solution was stirred for 6-8 hours, then dialyzed and freeze-dried.

By working in an analogous way and by using any suitable polymeric scaffold of the invention and any proper biotinylating moiety, biotinylated-cBSA and biotinylated-dextran can be obtained.

2) Derivatization of Biotinylated Alginate with Tn 14 mg (0.071 mmol) of biotinylated alginate were dissolved in 5.0 mL of 0.2 M MES buffer, pH 6.0. After solubilization, EDC (33.9 mg) and NHS (4.7 mg) were added and, after 10 min, 0.6 mg ($1.95 \times 10^{-3}$ mmol, 0.027 eq) of β-Gal-NAc-α-O-Ser. The solution was stirred for 8 h, dialyzed and freeze-dried and the title compound was recovered accordingly.

By working in an analogous way by starting with any biotinylated scaffolds as per step (1), those same biotinylated scaffolds can be also derivatised/conjugated with TF antigen.

Example 3

Determination of the Degree of Substitution of the Conjugated Compound of Example 1

The experimental conditions applied are those indicated by the supplier of the enzyme as stated in the above specification.

The molar substitution degree of the compound of previous Example 1 resulted to be 3%.

Example 4

Determination of the Degree of Substitution of the Conjugated Compound of Example 2

The determination of the degree of substitution of the conjugated compounds of the present invention, comprising alginate or dextran as the polymeric scaffold, is carried out by elemental analysis.

The molar substitution degree of the compound of previous Example 2 resulted to be 15%.

Example 5

Production and Selection of Anti-Tn and Anti-TF Antibodies

Anti-Tn and anti-TF antibodies were produced according to the preferred methods disclosed in the description of the invention and here below reported:

1) Two 8-week-old female BALB/c mice were immunized by 3 intraperitoneal injections of 200 μg of Tn-cBSA properly emulsified in Ribi's (MPL®+TDM Adjuvant System; Sigma); so as to observe the immune response. Three additional intravenous injections of 20 μg of the selected conjugate compound properly diluted in PBS followed;
2) animals were sacrificed and spleen excised;
3) antibody-producing cells were immortalized by somatic cell hybridization (fusion);
4) hybrid cells were selected in HAT culture medium;
5) ELISA test was performed to obtain the most specific clones; and
6) subcloning was performed.

Steps 2), 3), 4) and 6) of the above disclosed method were performed according to known methods (see the references in the former description of the invention).

Step 5) was performed according to the method disclosed in the following Example 6.

Example 6

Selection of Antibodies

ELISA test according to the method disclosed in the description of the invention was carried out as follows:
- the microtiter plate wells were coated with 10 μg/ml streptavidin in carbonate buffer 100 mM pH 9.6 over night at 4° C.;
- after a PBS wash the wells were filled with 100 μg/ml of Tn-biotinylated alginate conjugate and incubated for 1 h at 37° C.;
- washing with PBS was performed three times at room temperature;
- blocking with a PBS Ovalbumin, 1% solution for 1 h at 37° C.;
- washing with PBS was performed three times at room temperature;
- mouse serum hybridoma supernatant was added to the wells and incubated for 1 h at 37° C.;
- washing with a PBS Tween 0.02% solution for three times;
- anti-mouse IgG-HRP conjugated secondary antibody was added and incubated for 1 h at room temperature;
- washing with a PBS Tween 0.02% solution for three times at room temperature;
- 0.5 mg/ml ABTS peroxidase substrate was added;
- colorimetric quantification of bound antigen on ELISA plate at 405 nm.

The invention claimed is:

1. A compound comprising a plurality of Tn or TF antigens wherein each of said antigens consists of formula I or II:

Formula I (TF antigen)

Formula II (Tn antigen)

directly conjugated to a polymeric scaffold selected from the group consisting of cationized bovine serum albumin (cBSA), alginate and dextran.

2. A compound according to claim 1, wherein the polymeric scaffold is cBSA.

3. A compound according to claim 1, obtained by a process consisting essentially of the steps of:
a) dissolving any one of the polymeric scaffolds selected from the group consisting of cationized bovine serum albumin (cBSA), alginate and dextran, in a suitable buffered aqueous solution;

b) adding directly to the solution of step (1) a condensing agent and a suitable amount of Tn or TF antigens in the presence of a condensing agent; and
c) mixing and stirring the resulting solution from step (2) for a suitable period of time and recovering the obtained product.

4. A compound according to claim 1, wherein the antigens are Tn.

5. A vaccine against tumors comprising an effective amount of a compound according to any of claim 1, 2 or 3 or a pharmaceutical composition thereof.

6. A pharmaceutical composition comprising an effective amount of a compound of any one of claim 1, 2 or 3, together with a suitable solvent and with one or more pharmaceutically acceptable excipients.

7. A method for the treatment of tumors, comprising the administration to a mammal of an effective amount of a compound according to any one of claim 1, 2 or 3 or a pharmaceutical composition thereof.

8. A process for the preparation of a compound of any one of claim 1, 2 or 3, which process comprises the steps of:
   1) dissolving any one of the polymeric scaffolds in a suitable buffered aqueous solution;
   2) adding to the solution of step (1) a condensing agent and a suitable amount of Tn or TF antigens; and
   3) mixing and stirring the resulting solution from step (2) for a suitable period of time and recovering the obtained product.

9. A process for the preparation of anti-Tn antibodies or of anti-TF antibodies, comprising the steps of:
   1) BALB/c mice immunization
   2) sacrifice of the animals and spleen excision
   3) immortalizing antibody-producing cells by somatic cell hybridization (fusion)
   4) selection of the hybrid cells in HAT culture medium
   5) screening by ELISA assay to obtain the most specific clones
   6) subcloning;
wherein step (1) comprises injecting a compound according to any one of claim 1, 2 or 3.

10. An antibody produced according to claim 9.

11. An antibody according to claim 10 further functionalised with a therapeutic or diagnostic moiety.

12. A compound according to claim 3, wherein the suitable buffered aqueous solution is a buffering system for a pH of about 4.5 to about 7.

13. A compound according to claims 12, wherein the buffereing system is an aqueous solution comprising MES.

14. A compound according to claim 13, wherein the condensing agent allows carboxamido bonds.

15. A compound according to claim 14, wherein the condensing agent is selected form the group consisting of: N-Hydroxysuccinimide (NHS) and N-Hydroxysuccinimide (NHS) in combination with 1-ethyl-3-(3-dimethylaminopropyl)carbodiimide (EDC).

* * * * *